United States Patent
Duraffourg

(10) Patent No.: US 10,551,333 B2
(45) Date of Patent: Feb. 4, 2020

(54) HEAT FLUX SENSOR THAT IMPLEMENTS AT LEAST ONE OPTICAL RESONATOR, GAS SENSOR AND PIRANI GAUGE COMPRISING AT LEAST ONE SUCH SENSOR

(71) Applicant: Commissariat a L'Energie Atomique et aux Energies Alternatives, Paris (FR)

(72) Inventor: Laurent Duraffourg, Voiron (FR)

(73) Assignee: Commissariat a L'Energie Atomique et aux Energies Alternatives, Paris (FR)

(*) Notice: Subject to any disclaimer, the term of this patent is extended or adjusted under 35 U.S.C. 154(b) by 415 days.

(21) Appl. No.: 15/245,472

(22) Filed: Aug. 24, 2016

(65) Prior Publication Data

US 2017/0059499 A1    Mar. 2, 2017

(30) Foreign Application Priority Data

Aug. 28, 2015 (FR) ...................................... 15 58032

(51) Int. Cl.
*G01N 25/20* (2006.01)
*G01L 21/12* (2006.01)
*G01K 17/00* (2006.01)
*G01K 11/00* (2006.01)
*G01L 7/02* (2006.01)
(Continued)

(52) U.S. Cl.
CPC ............. *G01N 25/20* (2013.01); *G01K 11/00* (2013.01); *G01K 17/00* (2013.01); *G01L 7/026* (2013.01); *G01L 21/12* (2013.01); *G01N 33/0036* (2013.01); *G02B 6/29341* (2013.01)

(58) Field of Classification Search
CPC .... G01N 25/20; G01N 33/0036; G01L 21/12; G01L 7/026; G02B 6/29341; G01K 17/00; G01K 11/00
See application file for complete search history.

(56) References Cited

U.S. PATENT DOCUMENTS 5,336,324 A * 8/1994 Stall ...................... C23C 14/243
                                                                    118/715
7,616,850 B1   11/2009 Watts et al.
(Continued)

FOREIGN PATENT DOCUMENTS

WO    WO 2011/044547 A2    4/2011

OTHER PUBLICATIONS

French Preliminary Search Report dated Jun. 21, 2016 in French Application 15 58032 filed on Aug. 28, 2015 (with English Translation of Categories of Cited Documents).
(Continued)

*Primary Examiner* — Justin Seo
*Assistant Examiner* — John M Royston
(74) *Attorney, Agent, or Firm* — Oblon, McClelland, Maier & Neustadt, L.L.P.

(57) ABSTRACT

A heat flux sensor including at least one optical resonator, suspended on a support, the optical resonator intended to be suspended in a gaseous environment, at least one first device intended to introduce a measurement light beam into the waveguide, at least one second collection device, intended to collect a detection light beam coming from the optical resonator and a device for heating of the optical resonator.

25 Claims, 7 Drawing Sheets

(51) Int. Cl.
*G01N 33/00* (2006.01)
*G02B 6/293* (2006.01)

(56) References Cited

U.S. PATENT DOCUMENTS

| | | | | |
|---|---|---|---|---|
| 7,975,525 | B2* | 7/2011 | Bonne | G01N 33/0006 73/1.07 |
| 2004/0113104 | A1* | 6/2004 | Maida, Jr. | E21B 47/123 250/573 |
| 2004/0233458 | A1 | 11/2004 | Frick | |
| 2007/0269901 | A1 | 11/2007 | Armani et al. | |
| 2014/0157887 | A1* | 6/2014 | Viard | B81B 3/0081 73/204.17 |
| 2014/0283601 | A1* | 9/2014 | Bhave | G01P 15/093 73/504.12 |
| 2014/0321502 | A1* | 10/2014 | Ahmed | G01K 11/00 374/130 |
| 2014/0367687 | A1* | 12/2014 | Loncar | G02B 6/136 257/52 |
| 2016/0116678 | A1* | 4/2016 | Evans | G01J 1/4257 385/1 |

OTHER PUBLICATIONS

David C. Aveline, et al "Miniature Trace Gas Detector Based on Microfabricated Optical Resonators", Technology Focus: Sensors, 2013, 2 pgs.

F. T. Zhang, et al., "A micro-Pirani vacuum gauge based on micro-hotplate technology", Sensors and Actuators A 126, 2006, 6 pgs.

U.S. Appl. No. 13/702,790, filed Feb. 20, 2013, 2013/0144542 A1, Thomas Ernst, et al.

U.S. Appl. No. 14/030,205 filed Sep. 18, 2013, 2014/0076024 A1, Laurent Duraffourg, et al.

U.S. Appl. No. 14/029,920, filed Sep. 18, 2013, 2014/0079091 A1, Jeremie Ruellan, et al.

U.S. Appl. No. 14/519,390, filed Oct. 21, 2014, 2015/0107357 A1, Sebastien Hentz, et al.

U.S. Appl. No. 14/429,676, filed Mar. 19, 2015, 2015/0247828 A1, Jeremie Ruellan, et al.

U.S. Appl. No. 14/619,656, filed Feb. 11, 2015, 2015/0226713 A1, Jeremie Ruellan, et al.

U.S. Appl. No. 15/031,198, filed Apr. 21, 2016, Laurent Duraffourg, et al.

* cited by examiner

HEAT FLUX SENSOR THAT IMPLEMENTS AT LEAST ONE OPTICAL RESONATOR, GAS SENSOR AND PIRANI GAUGE COMPRISING AT LEAST ONE SUCH SENSOR

TECHNICAL FIELD AND STATE OF THE PRIOR ART

The present invention relates to a heat flux sensor that can be used to measure the concentration of a gas or to measure very low pressures, thus forming a Pirani gauge.

In general the term heat flux sensor refers to any sensor which measures the heat exchange between the body of the sensor, for example in the form of a membrane, and the fluid medium wherein the sensor is located.

A heat flux sensor is placed in an environment containing the component to be analysed, an analyte in a carrier gas in the case of a gas sensor, or simply a certain number of gas molecules in the case of a Pirani gauge whose purpose is to measure low pressures.

Document WO2011/044547 describes a TCD ("Thermal Conductivity Detector") which uses the variation in thermal conductivity to determine the composition of the gaseous environment in which it is located. The detector is located at the outlet of a chromatographic column. This TCD sensor comprises an extended support plate, a heating element located on the support plate. The voltage change is measured at the terminals of the heated support plate to determine the variation in the electrical resistance, which depends on the temperature of the support plate and which is representative of the thermal exchanges that take place between the support plate and the gaseous environment. These thermal exchanges depend on the composition of the gaseous environment.

The document "A micro-Pirani vacuum gauge based on a micro-hotplate technology" F. T. Zhang et al, *Sensors & Actuators A* 126 (2006) 300-305 describes a Pirani microgauge comprising a plate suspended by four long beams and two short, narrow beams. A heating element is provided on the plate.

The gas sensor and the Pirani gauge which exhibit this structure have a Limit of Detection (LOD) which remains greater than 1 ppm, in particular since the structure of this sensor, as well as that of the Pirani micro-gauge, do not allow a dynamic measurement method, i.e. which uses a modulated input signal, to be implemented. This is due to their thermal time constant which is too great in relation to the modulation frequency. For example, for biomedical applications, for environmental or interior air quality monitoring it is sought to achieve a limit of detection less than 1 ppm.

DESCRIPTION OF THE INVENTION

Consequently an aim of the present invention is to provide a heat flux sensor, in particular such as a gas sensor or Pirani gauge, which can exhibit a limit of detection which is lower in comparison with sensors of the state of the art.

The above stated aim is achieved by a heat flux sensor which comprises at least one optical resonator, means for heating the optical resonator and means for measuring the variation of a characteristic of the optical resonator as a function of the variation of the composition of the environment wherein the sensor is located.

The temperature has an influence on the effective optical index of the optical resonator. Modification of this index alters the resonance frequency of the optical resonator, which may be measured from the wave that is transmitted or reflected by the optical resonator. This is linked to the variation in the thermal conductivity of the gaseous environment, for example of the gas mixture, and therefore to its composition.

In other words, the heat flux sensor uses an optical resonator as an element which is sensitive to heat exchanges with the surrounding gaseous environment.

The heat flux sensor according to the invention exhibits a limit of detection which is lower in comparison with those of the state of the art. A ratio 10 may be achieved.

The optical resonator is suspended by suspension means, which are configured to thermally isolate the resonator.

A measurement method using a continuous beam of light or a dynamic method using an amplitude modulated beam may be used. The thermal flux sensor according to the invention is particularly well suited to a dynamic measurement method, since the time required for its thermalisation is short. This is referred to as a low thermal constant. The sensor therefore offers an even lower limit of detection. Furthermore, the sensor exhibits a greater dynamic measurement range, i.e. it can detect temperature variations over a wider range, for example several tens of degrees.

In one embodiment, heating of the resonator is achieved by Joule effect type heating means located away from the optical resonator.

In another embodiment, the heating of the resonator is self-heating achieved by introducing a light beam which has sufficient power to heat the resonator into the optical resonator.

The subject-matter of the present invention is therefore a heat flux sensor comprising at least one optical resonator, suspended on a support, said optical resonator being intended to be suspended in a gaseous environment, said optical resonator comprising at least one waveguide, at least one first means intended to introduce a measurement light beam into the waveguide, at least one second collection means, intended to collect a detection light beam coming from the optical resonator waveguide and means for heating said optical resonator.

In one embodiment the heating means are located away from the optical resonator. The distance separating the heating means and the optical resonator is, for example, between 200 nm and 10 μm.

The means of heating may be Joule effect means of heating. In one embodiment example the means of heating may comprise at least one conductive wire suspended on said support, the wire being connected to a source of electrical voltage or of electrical current. In another embodiment means, the means of heating comprise at least one layer of electrical resistance material located facing the optical resonator and arranged on the support, the layer of electrical resistance material being connected to a source of electrical voltage or of electrical current.

In another embodiment, the means of heating comprise a light beam source configured to introduce a light beam into the optical resonator and whose power causes self-heating of the optical resonator.

According to an additional characteristic, the optical resonator is suspended on the support by at least one beam. The beam for example has a width of between 50 nm and 10 μm with a thickness of between 50 nm and 500 nm and a length of between 1 μm and 100 μm.

The optical resonator may comprise an optical ring, an optical disk or a photonic crystal.

In the case of an optical resonator comprising a ring, the latter may have a radius of between 1 μm and 100 μm.

In one embodiment example, the first means for introducing a measurement light beam into the optical resonator is a waveguide and the second collecting means is formed by the same waveguide as that of the first means, collecting a reflected light beam.

In another embodiment example, the first means for introducing a measurement light beam into the optical resonator is a waveguide and the second collecting means is formed by another waveguide, collecting a transmitted light beam.

In another embodiment example, the first means for introducing a measurement light beam into the optical resonator is a waveguide and the second collecting means collecting a reflected light beam is formed by the waveguide of the first means, and wherein said sensor also comprises another waveguide collecting a transmitted light beam.

In the present application, the term "transmitted beam" refers to a beam that is collected by a means of collection, for example a waveguide, which is different from the means of introduction, for example a waveguide, and the term "reflected beam" refers to a beam that is collected by the means of introduction, for example by the introduction waveguide.

Another subject-matter of the invention is a gas sensor comprising at least one thermal flux sensor according to the invention, the optical resonator being suspended in a fluid channel between an input supplying a gas mixture to the fluid channel and an output removing said gas mixture from the fluid channel.

Another subject-matter of the invention is a Pirani gauge comprising at least one heat flux sensor according to the invention, the optical resonator being suspended in a gaseous medium volume whose pressure it is sought to measure.

Another subject-matter of the present invention is a measurement system comprising at least a sensor according to the invention, a measurement light beam emitter connected to the first means, at least one photodetector connected to the second means and electronics for processing the signals emitted by the photodetector.

The measurement light beam emitter may emit an amplitude modulated beam.

The measurement light beam emitter is for example a laser.

According to one embodiment example, the measurement light beam emitter also forms the light beam emitter which is used for self-heating of the optical resonator.

The measurement system may comprise another gas sensor according to the invention, the fluid channel of one of the sensors being designed to be supplied with a gas mixture and the fluid channel of the other sensor being supplied with the carrier gas alone, the second means of collection of each sensor being connected via a photodetector to the processing electronics in order to allow a differential measurement.

The measurement system may comprise another gas sensor according to the invention, the fluid channel of one of the sensors being supplied with a gas mixture and the fluid channel of the other sensor being supplied with the carrier gas alone, the second means of collection of each sensor being connected, via a recovery and interference device for the measurement light beams emerging from the two sensors, to the processing electronics in order to allow the phase-shift between the detection beams collected by the two means to be measured so as to allow an interference measurement to be made.

BRIEF DESCRIPTION OF THE DRAWINGS

The present invention will be better understood on the basis of the description which follows and the appended drawings, in which.

DETAILED DESCRIPTION OF SPECIFIC EMBODIMENTS

The heat flux sensor according to the invention is intended to be placed in a gaseous environment for example, either to analyse the composition of a mixture of gases or to measure a pressure level.

In the examples that follow, the heat flux sensor is described in its application as a gas sensor. It is therefore intended to be immersed in a mixture of gases to be analysed which are flowing through the fluid channel, where the mixture of gases comprise a carrier gas such as helium and one or more analytes to be analysed.

The heat flux sensor may form a Pirani gauge. It may for example be arranged in an enclosure and used to monitor the vacuum level in the enclosure.

In general the sensor is placed in a volume of gas.

Figure 1:
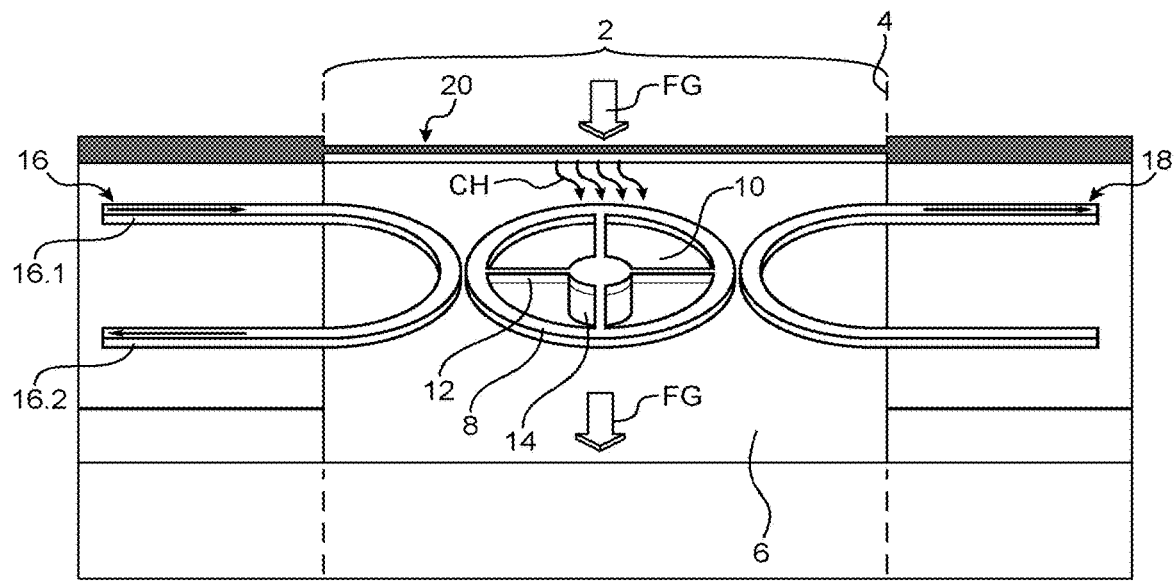
FIG. 1 is a perspective view of an embodiment example of a heat flux detector according to a first embodiment.
Figure 2:
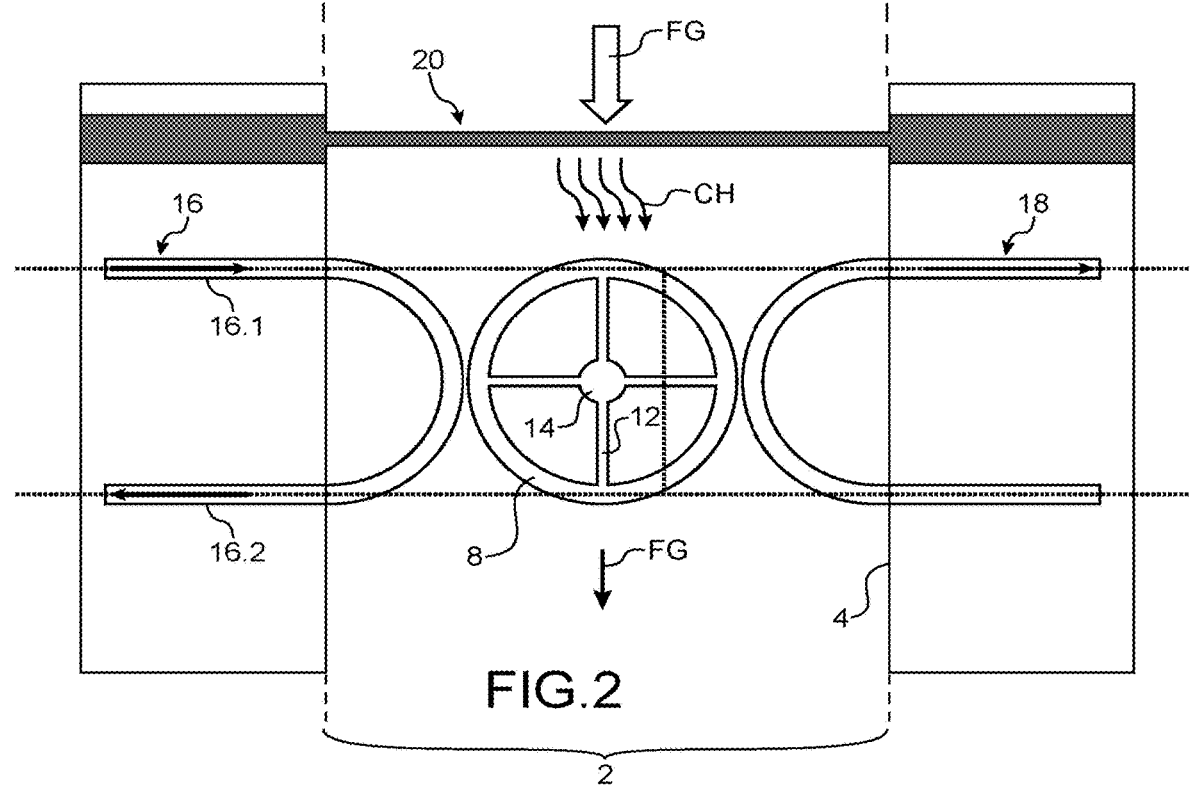
FIG. 2 is a top view of the sensor of FIG. 1.

In FIGS. 1 and 2 there can be seen an example of a heat flux sensor according to a first embodiment arranged in a fluid channel 2, where the channel 2 comprises lateral walls 4 linked by a transverse wall 6 which forms the bottom of the channel 2. The channel 2 is for example closed by a cover 7 which is visible in FIG. 6.

The channel 2 comprises an end intended for supplying gas and an end intended for removing the gas. The gas flow is represented by the arrows FG.

The sensor comprises an optical resonator 8 which is thermally insulated from the channel walls, so as to limit thermal losses by diffusion towards the support which could reduce its sensitivity. It is preferably also optically isolated from the channel walls.

The optical resonator 8 is advantageously suspended in the channel 2 by means of suspension 10. In the example shown, the optical resonator 8 comprises a waveguide which forms an optical ring. The means of suspension used comprise four arms 12 linking the interior edge of the ring to a pin 14 which forms part of the bottom 6 of the channel. The cross-section of the arms 12 is chosen so that it is sufficiently small to limit thermal losses, and is for example between 1 nm and 1 μm. Generally the arms are made of the same material as the resonator. Furthermore the material of the pin 14 is advantageously chosen so that it exhibits low thermal conductivity, for example it is made of $SiO_2$, SiN, SiC etc. In order to limit thermal losses and to thus ensure good thermal insulation, the pin is advantageously made of oxide, for example of $SiO_2$, which exhibits low thermal conductivity.

Other examples of means of suspension can be envisaged, for example they may comprise beams extending between the external edge of the resonator and the channel side walls.

The resonator may comprise a photonic crystal, for example by making holes in the waveguide.

Alternatively, the optical resonator may comprise a waveguide formed by an optical disk or an optical torus or again a photonic crystal, each being suspended by the means of suspension described above.

Advantageously, holes of a few tens of manometers in diameter separated by a few tens of manometers are made in the means of suspension, thus providing both thermal insulation and optical isolation of the resonator relative to the support.

The sensor also comprises at least one waveguide 16 of which at least one part is arranged close to the optical resonator in order to introduce a measurement light beam, called the probe beam, into the latter and to recover a transmitted or reflected light beam, called the detection beam.

In the example shown, the sensor comprises a first waveguide 16 which is U-shaped. One branch 16.1 of the U comprises a free end intended to be linked to a light source and to introduce the light into the optical resonator 8 at the bottom of the U. The other branch 16.2 of the U collects the light reflected through its free end, for example intended to be connected to a photodetector.

The sensor comprises a second waveguide 18 which is in this example also U-shaped, intended to collect the light transmitted by the resonator. The second waveguide 18 is arranged on the other side to the first waveguide 16 in relation to the resonator. In these examples the bottoms of the U overhang into the channel in order to be as close as possible to the resonator.

The sensor also comprises means 20 for heating the optical resonator, which are located away from the resonator. In the example shown this is an electrically conductive wire connected to a current source or a voltage source. The wire is made for example of metal or of semiconductor material, such as silicon. In this example and advantageously the wire is suspended, between the two lateral walls of the channel, transversely to the gas flow FG. It is preferably placed in the plane containing the optical resonator.

The heat produced by the wire 20 is symbolically represented by the arrows CH.

Alternatively the heating wire could extend parallel to the gas flow.

In the example shown, the wire is placed in the plane of the resonator. It could be arranged in a plane that is parallel to and distinct from the plane of the resonator, however this embodiment is more complex.

Several electrical conductor wires could be envisaged.

The wire produces heat by the Joule effect, which will heat the optical resonator by thermal conduction and by radiation.

For example, for a channel of width and of height typically between 10 μm and 200 μm, for example of width 100 μm and of height 100 μm, and a resonator of diameter of between 10 μm and 100 μm, for example 50 μm, the distance between the wire and edge of the resonator is of the order of a few μm, for example between 200 nm and 10 μm.

Figure 3A:
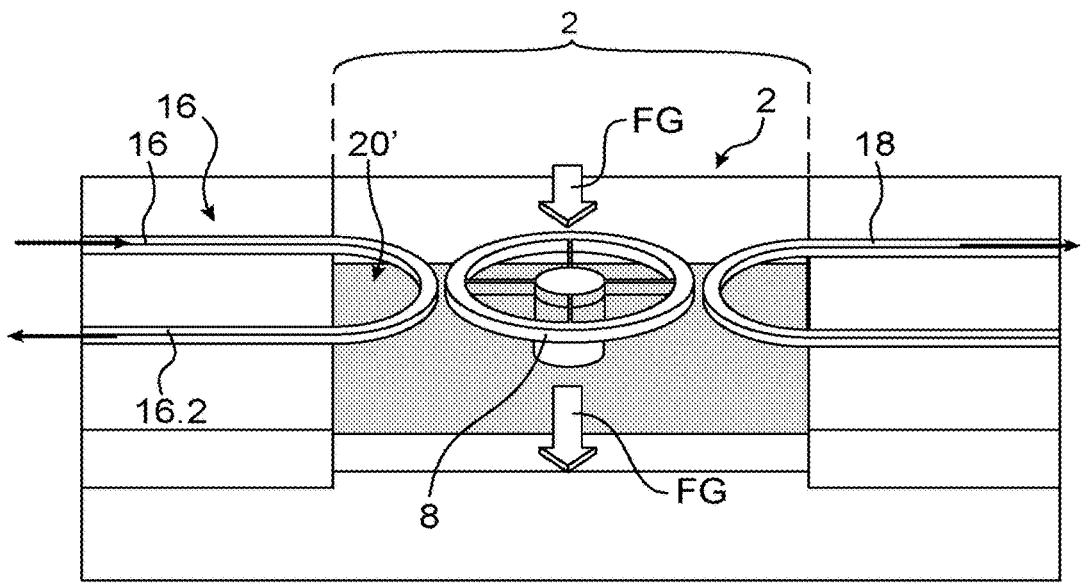
FIG. 3A is a perspective view of another embodiment example of a heat flux detector according to a first embodiment.
Figure 3B:
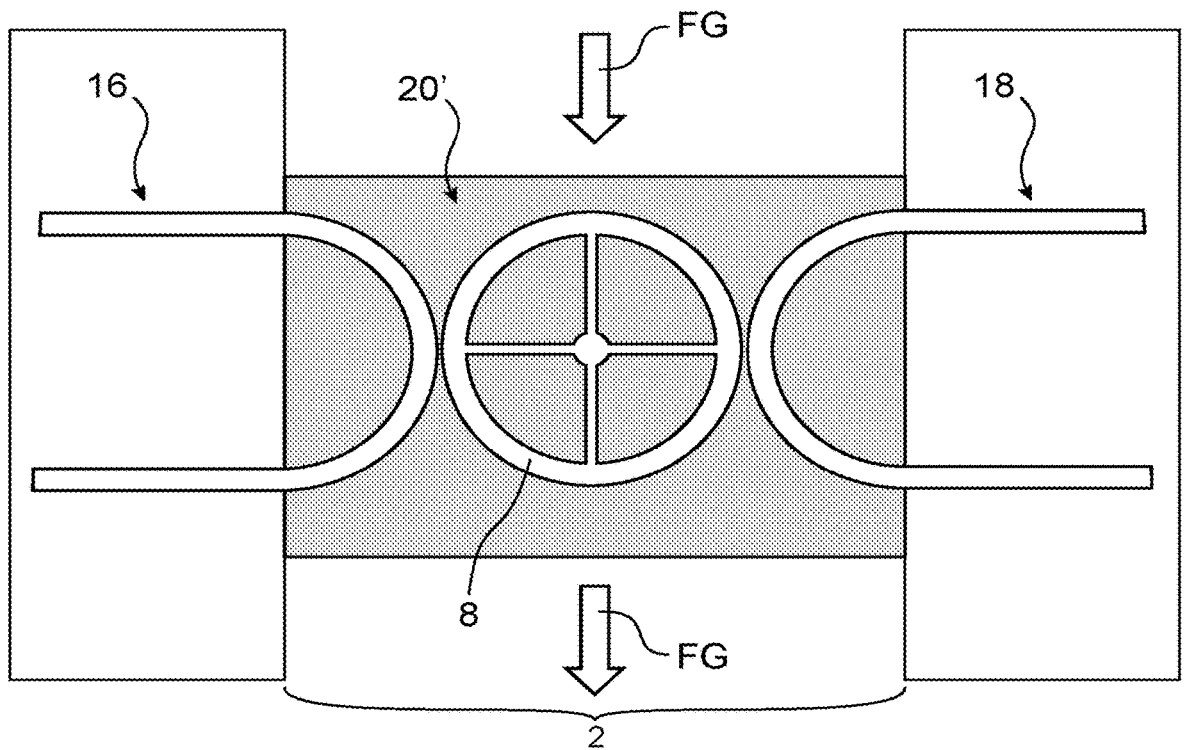
FIG. 3B is a top view of the sensor of FIG. 3A.

In FIGS. 3A and 3B there can be seen another embodiment example of a heat flux sensor according to the first embodiment, wherein the means of heating are formed by a resistive layer 20' arranged in a plane parallel to the optical resonator and close to the resonator in consideration of the gas flow. In the representation in FIG. 3A, the resistive layer is located beneath the resonator. The layer is deposited on the transverse wall of the channel and is connected to a source of voltage or of current. The resistive layer advantageously exhibits at least one surface that is sufficient to ensure that a projection of the resonator onto the plane of the resistive layer is included within the resistive layer 20'.

The resistive layer 20' is made, for example, of TiN or of W.

This embodiment example offers the advantage of heating the resonator more uniformly and more rapidly. Furthermore the temperatures reached may be higher, which allows limits of detection lower than those of the sensor in FIGS. 1 and 2 to be achieved.

In the examples described, a single optical resonator is used, but the use of several coupled resonators can be envisaged, for example by arranging them in the same plane or in two different planes, for example two parallel planes, for example where the planes are parallel to the flow in the channel. For example two resonant rings may be coupled.

Figure 6:
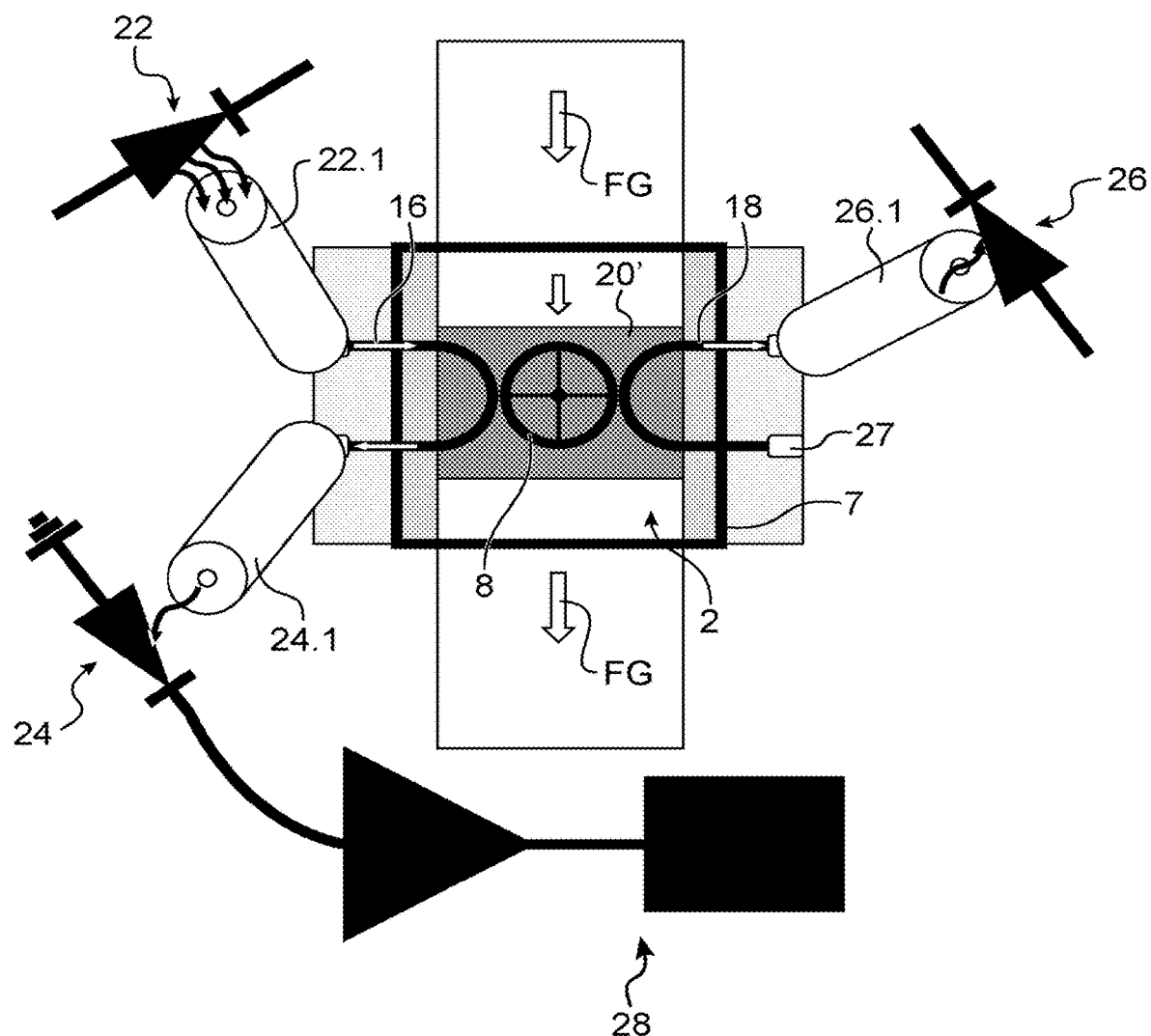
FIG. 6 is a schematic representation of a measurement system comprising a thermal flux sensor of FIG. 3A.

In FIG. 6, there can be seen a schematic representation of a measurement system according to the invention which comprises a heat flux sensor of FIGS. 3A and 3B, an optical emitter 22, for example a laser source, connected to an input of the branch 16.1 of the first waveguide 16 and intended to introduce light into the resonator, a first photodetector 24, for example a photodiode, connected to the outlet from the branch 16.2 of the first waveguide 16 to collect the reflected beam, a second photodetector 26, for example a photodiode, connected to the outlet from the second waveguide 18 to collect the transmitted beam. A coupling network 27 is connected to the input of the second waveguide 18. The network allows the effective coupling of the light emerging from the source, generally a laser source, into the introduction waveguide. The same network also allows decoupling of the light emerging from the waveguide so that it is collected on the photodetector.

The introduction of the light into the two waveguides 16 and 18 and recovery of the reflected light in the two waveguides 16 and 18 and comparison of the signals obtained could be envisaged.

The inlet to the channel 2 is for example connected to the outlet from a gas chromatographic or capillary connected to a gas mixture source.

The optical emitter 22 and the photodetectors 24, 26 are for example connected to waveguides by optical fibres 22.1, 24, and 26.1 respectively.

It should be recalled that a single photodetector suffices, and that collection of the transmitted or reflected beam is sufficient.

The photodetectors 24 and 26 are connected to processing electronics 28 which determine the composition of the gas mixture from the signals transmitted by the photodetector or photodetectors.

The operation of the heat flux sensor of FIGS. 1 and 2, used as a gas sensor, will now be described. The operation of the sensor of FIGS. 3A and 3B is similar to those of FIGS. 1 and 2.

We will consider a gaseous mixture comprising a carrier gas, for example helium or hydrogen, and at least one analyte.

Preferably, a carrier gas is chosen such that it has the property of having a large thermal contrast relative to the analytes, so as to maximise the difference between the temperature with the carrier gas alone and the temperature in the presence of the carrier gas/analyte mixture. In order to achieve this, a carrier gas is chosen for example which has a thermal conductivity k which is much greater than those of the analytes.

The table below lists the thermal conductivity values for air and helium and two analytes pentane and benzene.

| | Gas | | | |
|---|---|---|---|---|
| | $H_2$ | Helium | Air | Pentane | Benzene |
| kgaz (mW/m · K) | 168 | 143 | 24 | 15 | 8 |

In a first step the gas mixture flows through the channel around the resonator. The wire is supplied with continuous current or voltage, the optical resonator is then heated by thermal conduction and radiation. The gas mixture has a stable composition. A thermal balance is established, and the resonator then has a temperature T.

Considering that the composition of the gas mixture is stable in channel, the resonator is heated to a given temperature which results from a thermal equilibrium between the flow of heat from the heating wire by conduction and radiation and heat losses through exchange with the support forming the thermostat through the gas mixture and through the means of suspension.

The power provided $P_J$ by the wire 20 by the Joule effect is expressed as:

$$P_J = R_0 I^2$$

Where $R_0$ is the electrical resistance of the conductive wire 20, I the value of the electrical current passing through it.

Figure 9:
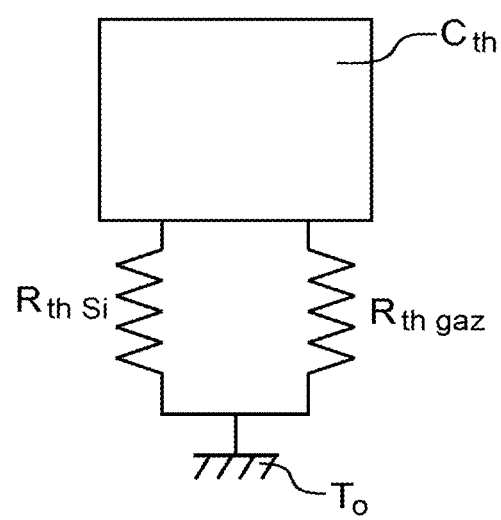
FIG. 9 is a representation of the equivalent thermal circuit of the system formed by the support and the thermal resonator.

The heated optical resonator can be compared to a thermal capacitance $C_{th}$ connected to a thermostat by means of a thermal resistance as shown schematically in FIG. 9. The optical resonator is surrounded by a gas.

The thermal resistance $R_{th}$ which characterises the exchange between the resonator and the exterior is made up of the thermal resistance of the gaseous environment $R_{th\text{-}gaz}$ and the thermal resistance of the suspension arms of the resonator, made for example of silicon, $R_{th\text{-}Si}$.

At thermal equilibrium the optical resonator is at a stable temperature T which is expressed as:

$$T = T_0 + P \cdot R_{th} \quad (I)$$

$T_0$ is the temperature of the walls of the channel and that of the optical resonator in the absence of heating.

Considering a gaseous mixture containing the carrier gas and an analyte, the thermal conductivity of the gas mixture is expressed as:

$$\kappa gaz = \kappa 1 c + \kappa 2 (1-c)(W \cdot m^{-1} \cdot K^{-1}) \quad (III)$$

Where k1 is the thermal conductivity of the analyte,
C is the concentration of the analyte
k2 is the thermal conductivity of the carrier gas.

For information, the relative variation in the thermal conductivity is 1 ppm for 1 ppm of relative variation of the concentration of the analyte concentration in the carrier gas.

A probe beam, which is for example continuous, is introduced into the resonator via the first waveguide. The wavelength (or the frequency $F_s$) of the probe beam is offset in relation to the wavelength corresponding to the transmission or reflection maximum, as is shown schematically in the representation of the transfer function H of an optical resonator as a function of its frequency in Hz in FIG. 4. An amplitude modulated probe beam can also be introduced into the resonator to carry out a dynamic measurement, as will be described below.

During a second step, the analyte concentration varies.

In accordance with the relationship (III), the thermal conductivity of the gas mixture varies and the thermal exchanges between the optical resonator and the gas mixture are modified, which modifies the thermal equilibrium and the temperature of the thermal resonator.

The variation in the temperature of the optical resonator is estimated using the equation for the diffusion of heat through this mixture and in the attachments holding the optical resonator, the temperature variation can be expressed as:

$$\Delta T = P/G$$

Where P is the power dissipated as a result of the Joule effect, where G represents the thermal conductance of the system and contains a term relating to the exchanges through the gaseous medium and a term relating to the exchanges through the materials forming the means of suspension and the pin, where appropriate, and where the other dissipation modes are assumed to be negligible: G can then be expressed as G=Ggaz+Gs, where Gs designates the conductance of the silicon which forms the resonator and the means of suspension.

Where $Ggaz = \kappa(S/g) \times \gamma$

Ggaz is calculated by considering two facing planes, for example a plane which contains the resonator such as a disk, a ring or a photonic crystal facing the substrate placed underneath. S is the equivalent surface area of the resonator, δ is a unit-free correction factor which allows for the fact that diffusion is not achieved simply through perpendicular flows. This coefficient depends furthermore on the distance g between the two planes. Moreover, as has been mentioned previously, the sensor is preferably such that the thermal conductance through the resonator suspensions or resonator attachment is small in relation to the conductance through the gas. By considering thin suspensions, and the pin being made of thermally insulating material, the ratio Gs/Ggaz may be less than 1% and the conduction term through the attachment therefore becomes negligible.

The transfer function of the temperature variation as a function of conductivity, $\delta T \delta \kappa gas/$ around an initial concentration $c_0$ may be expressed as $$\partial \Delta T / \partial \kappa gaz \tilde{\ } (gP/S\gamma\kappa^2_{gaz})_{T=T0, c=c0}$$

Its value depends on the value of the distance g and on the power introduced in order to heat the optical resonator. For example by considering g to be of the order of 1 μm. This expression leads to a typical value of the relative variation of the temperature as a function of the conductivity:

$$\kappa gaz/\Delta T \times \partial \Delta T/\partial \kappa gaz \tilde{\ } 1$$

This variation in the temperature of the resonator causes a variation in the effective optical index of the resonator.

Consequently by heating the optical resonator the effective optical index is modified, the value at thermal equilibrium is designated a "nominal value"

The variation of the optical index as a function of the temperature depends on the wavelength and on the temperature $T_0$, which is the thermal operating point which corresponds to the temperature with the carrier gas only (without analyte).

When the composition of the gas mixture changes, the thermal conductivity of the gas mixture changes. This implies that the thermal exchanges between the means of heating and the optical resonator, and between the optical resonator and the support, are modified. The thermal equilibrium is modified and the temperature of the resonator increases or decreases, the effective optical index undergoes a variation δn around a nominal value, which is schematically represented in the representation of the transfer function of FIG. 4.

The optical resonance frequency of the resonator depends on the effective optical index. The modification of the effective optical index therefore causes a variation in the optical resonance frequency of the resonator.

The overall effect on the optical resonance frequency can be estimated through the relative variation of the resonance frequency as a function of the temperature:

$$1/\nu R \times \partial \nu_R / \partial T \, 50 \text{ ppm}$$

It should be noted that the variation in the resonance frequency of the resonator has several origins which are, in particular, the variation in the effective refractive index, the variation in the propagation length due to expansion of the resonator and variation of the thermal stresses of the layer. For example, in the case of silicon, the typical coefficient of expansion of silicon is 3 ppm and the variation in the effective refractive index of a silicon guide for a wavelength of 1.55 μm is of the order of 50 ppm. The first order variation of the effective refractive index is therefore the predominant effect. In the remainder of the description, it will be considered therefore that the variation of the effective optical index is the principal cause of the variation in the resonance frequency of the resonator.

The transfer function therefore moves along the abscissa as a function of the temperature of the optical resonator i.e. the resonance frequency which corresponds to the peak maximum varies. This variation is expressed as a modulation of the amplitude of the detection light intensity which is the transmitted or reflected signal. This resonance frequency variation modulates the optical intensity transmitted or reflected by the resonator.

Figure 4:
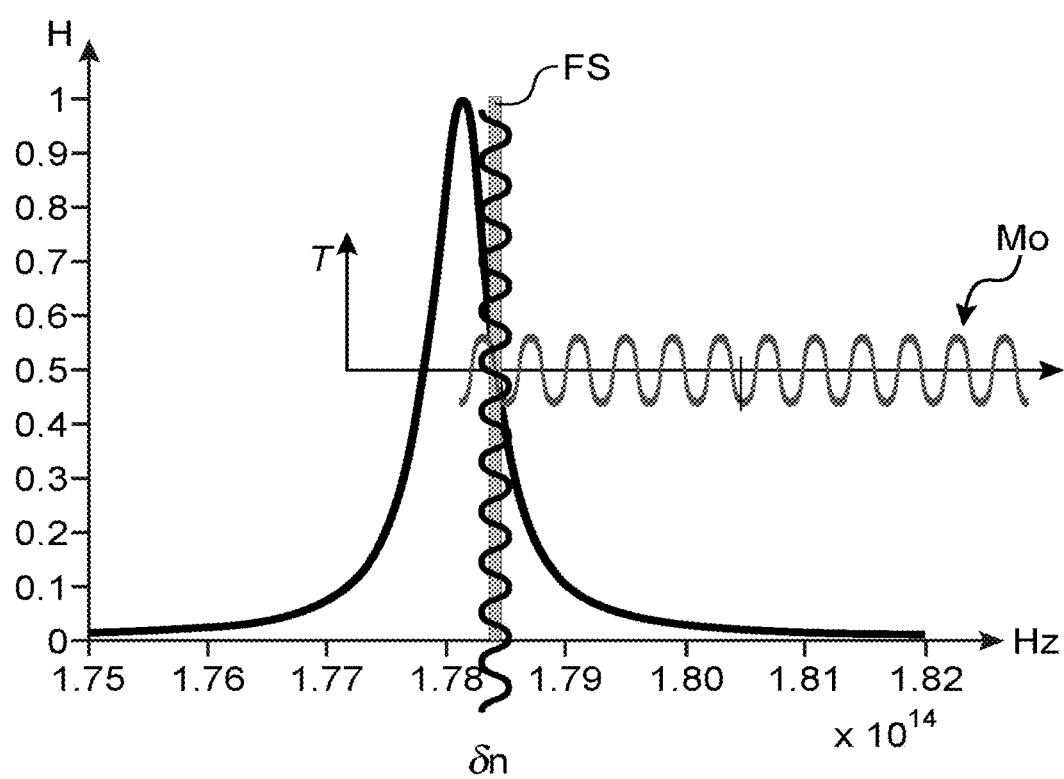
FIG. 4 is a representation of the transfer function of an optical resonator.

This modulation Mo is schematically represented in the transfer function of FIG. 4.

By measuring this modulation it is possible to relate back to the offset of the optical resonance frequency and to the transmitted or reflected optical intensity. It is therefore possible to determine the conductivity of the gas mixture. The greater the quality factor of the optical resonator, the greater the variation in light intensity. By knowing the components of the gas mixture and their thermal conductivities, it is possible to relate back to the composition of the gas mixture i.e. to the variation in the concentration of the analyte or analytes.

By limiting the thermal losses through the means of suspension, one can ensure that the main cause of temperature variation is due to the variation in the composition of the gas mixture.

The heat flux sensor according to the invention exhibits a very low thermal constant, and therefore very advantageously allows a dynamic measurement method to be implemented. Synchronous detection can then be operated by modulating the intensity of the light introduced. In this case a synchronous detection amplifier is used to demodulate the signal from the photodiodes. This minimises the impact of noise to 1/f and allows a greater ratio between the signal and continuous background noise to be achieved. The limit of detection of the sensor according to the invention can be lowered further. Moreover, it exhibits a greater dynamic range.

Figure 7:
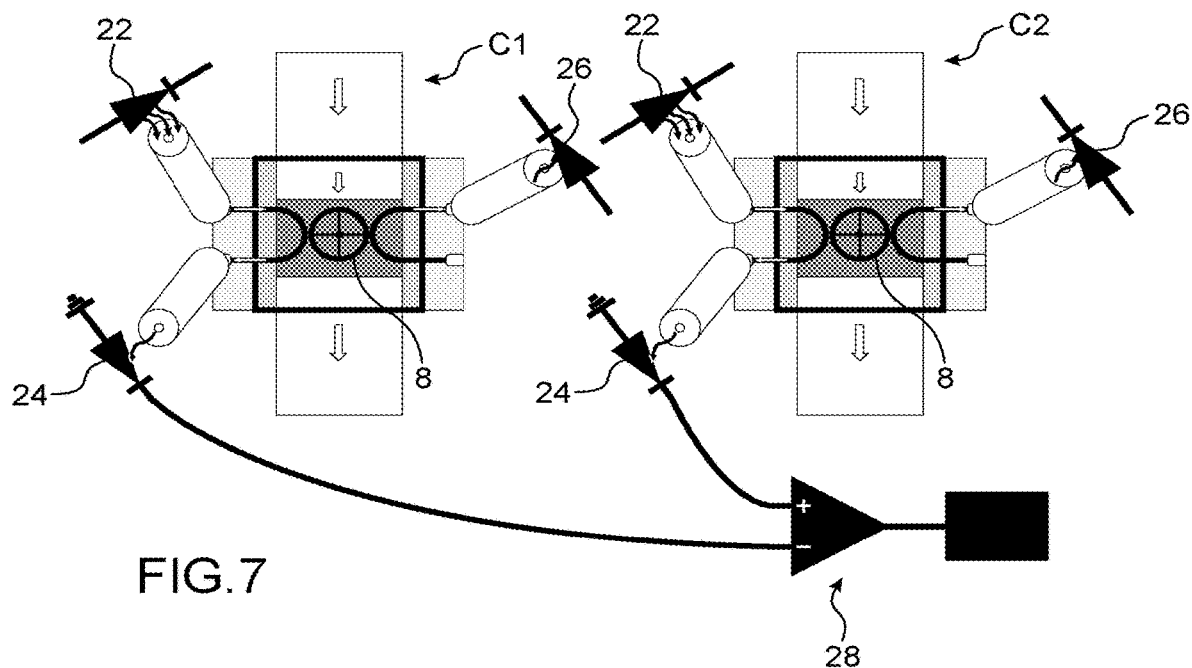
FIG. 7 is schematic representation of a measurement system configured to carry out differential measurement.

FIG. 7 shows an embodiment example of a system capable of differential measurement.

The system comprises two heat flux sensors according to the invention C1 and C2 each having its own fluid channel. The system comprises an optical emitter for each sensor or an emitter for both sensors and one or more photodetectors for each of the sensors.

The fluid channel of the sensor C1 is only supplied with carrier gas and the fluid channel of the sensor C2 is supplied with carrier gas only or with a gas mixture to be analysed (carrier gas and analyte).

The photodetectors of the two sensors are connected to the same processing electronics. Thus the differences in the electrical signals obtained by the photodetectors of the two sensors can be measured, which allows the continuous background noise to the removed and limits thermal drift to the first order.

Figure 8A:
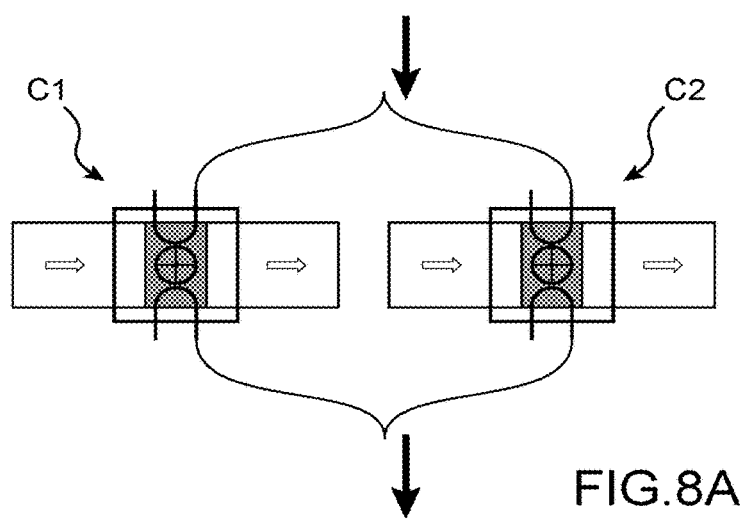
FIGS. 8A and 8B are schematic representations of systems configured to carry out interference-based measurement.
Figure 8B:
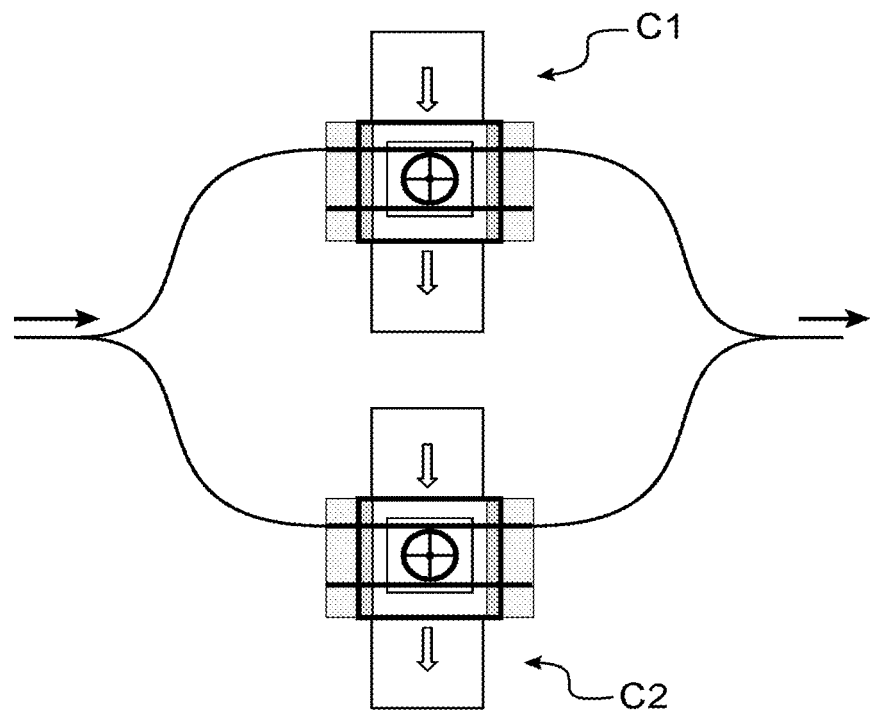

Another example of a measurement system can be seen in FIGS. 8A and 8B which advantageously implements an interference-based method in an interference structure, for example of the Mach-Zhender type.

As with the system in FIG. 7, the measurement system comprises two heat flux sensors C1 and C2 according to the invention, each having its own fluid channel. The system comprises an optical emitter 22 for both sensors and a photodetector which collects the detected light after interference.

The fluid channel for sensor C1 is only supplied with carrier gas and the fluid channel of the sensor C2 is supplied either with carrier gas only or with a gas mixture to be analysed (carrier gas and analyte).

The transmitted beams collected in the two sensors are combined and the resulting beam is processed by the electronics.

In FIG. 8A the sensors are of the same type as those in FIGS. 3A and 3B and in FIG. 8B the sensors comprise straight wave guides. Moreover the interference structure comprises, in this example, waveguides for recovering the measurement light beams coming from the two sensors. These waveguides are assembled as a "Y" to allow said measurement beams to interfere with each other. Naturally any other device for recovery and interference of the measurement light beams coming from the two sensors may be used, instead of the waveguides in a "Y" configuration.

In this system, the phase-shift of a branch of a Mach-Zhender relative to a branch of the other Mach-Zhender is measured, rather than the signal amplitude.

As a variant, the system can cause the reflected beams to interfere.

Since the interference-based system is an entirely optical differential mode, simpler electronics can be used and a more compact system can thus be made.

Figure 5:
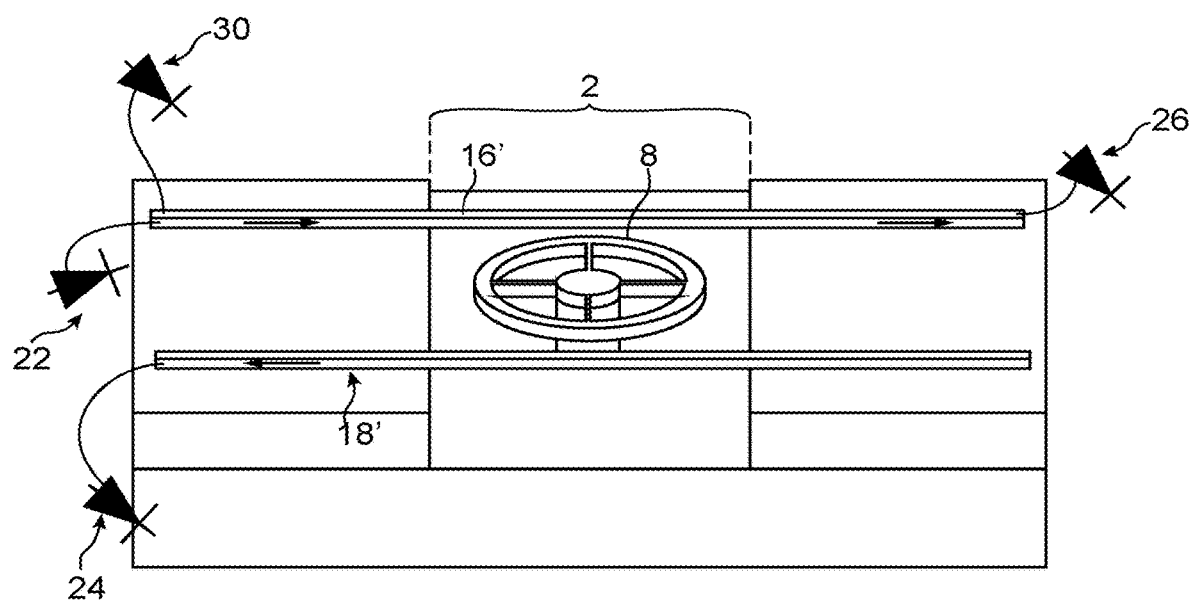
FIG. 5 is a perspective view of an embodiment example of a heat flux detector according to a second embodiment.

FIG. 5 shows an embodiment example of a sensor according to a second embodiment. This sensor differs from the sensors of the first embodiment by the fact that it does not comprise external heating means.

The sensor comprises a light source 30 connected to the first waveguide 16' which can ensure self-heating of the optical resonator 8 suspended in the channel 2. The waveguide 16' collects the transmitted light and the waveguide 18' collects the reflected light.

In this embodiment example the guides 16' and 18' are parallel and pass across the channel. Wave guides identical to the waveguides 16 and 18 may be envisaged. In the example shown, there is an additional light source involved, in relation to the light source 22, which sends a light beam of sufficiently high power into the first wave guide. The absorption mechanism transforms this optical energy into thermal energy, heating the resonator.

The local heating can range from a few degree for low powers, for example less than 100 μW, to several hundred degrees for high powers, for example of the order of ten or so mWatts or of several tens of mWatts.

The additional source of light 30 is for example a laser whose emission wavelength can be different to the wavelength of the sensor source.

As a variant, a single source of light can be used which introduces the sensor beam, both for measurement and for heating the resonator.

In this embodiment, when the thermal conductivity of the gas mixture surrounding the resonator varies, only the thermal exchanges between the resonator and the support formed by the channel are affected, since the heating is internal to the resonator.

The operating principle of the sensor according to the second embodiment is similar to that according to the first embodiment.

The temperature T of the resonator is the result of a thermal equilibrium between the increase in temperature and the thermal exchanges with the gaseous environment and may be expressed as:

$$T = T_0 + \Delta T = T_0 + opt/(G_{th\_Si} + G_{th\_gaz})$$

Where $T_0$ is the initial temperature of the resonator $P_{opt}$ is the power supplied by the heating light source.

$G_{th\_Si}$ and $G_{th\_gaz}$ are the thermal conductance of the silicon and of the gas respectively. Gth_Si characterises the exchanges through the suspension means.

The variation in the optical resonance frequency is measured. This varies as a function of the temperature of the resonator, which depends on the exchanges with the gaseous environment and therefore on its composition.

We will estimate the performance of the measurement sensor according to the invention. Let us consider that the lower limit of resolution is given by the smallest measurable spectral variation corresponding to the half-height width of a peak of the transmission or reflection response and considering a micro-resonator made of silicon with a fineness F=1000, with an effective index neff=2.4, and of radius R=50 μm, that is, a free spectral interval of the order of 3.2 nm. The half-height width will therefore be of the order of 3.2 pm, which corresponds to a quality factor of $10^5$. The sensitivity of the resonance wavelength to the temperature being of the order of 75 ppm/° C. (that is ~50 ppm for a sensor wavelength of 1.55 μm), the theoretical temperature resolution is of the order of 0.05° K (that is: δΔT=0.05°).

For an operating temperature of 200° C. it is determined that the smallest measurable variation in concentration is from 200 ppb to 1000 ppm. The absolute detection limit depends on the carrier gas-analyte combination. In the case of benzene in helium, the detection limit is of the order of 7 ppm. TCDs of the state of the art can detect variations in concentration of benzene of from 10 ppm to a few tens of ppm, or even a hundred or so ppm.

It should be noted that this calculation does not take into consideration noise inherent to the source (photon noise) and to the detector (Shottky noise, 1/f . . . ) but only of the spectral fineness of the optical resonator.

Dimensioning values will therefore be given by way of examples only.

The width of the waveguide may be between 100 nm and 500 nm for a height of between, for example, 100 nm and 500 nm. The waveguide has for example the following dimensions 500 nm×200 nm.

The distance between a waveguide and the optical resonator is for example between 50 nm and 500 nm, for example equal to 200 nm.

The distance between the heating element and the resonator is of the order of 1 μm and may reach several microns, and is for example equal to 2 μm.

In the case of an optical resonator of the ring type its radius may be between 1 μm and 100 μm, and for example equal to 50 μm.

For example the optical resonator or resonators may be made of silicon, of doped silicon, of silicon nitride, of lithium niobate or of GaAs based III/V materials. The wavelength of the laser or lasers forming the emitters is adapted according to the guide materials and dimensions, in particular according to their cross-section and as a function of the radius of ring or disk resonators. For example, in the case of an optical resonator made of silicon or of III/V materials the wavelength is 1.55 μm, in the case of an optical resonator made of SiGe alloy, the wavelength ranges from about 3 μm to 7 μm, in the case of an optical resonator made of Ge the wavelengths will be in a range 7 μm-12 μm The thermal sensor may be realised using methods known in microelectronics, for example from an SOI (Silicon on Insulator) substrate, in particular by applying lithography, etching, epitaxial growth steps.

The invention claimed is:

1. A heat flux sensor comprising:
at least one optical resonator suspended on a support by
at least one suspension element configured to thermally isolate the suspension element from the support, said optical resonator being configured to be suspended in a surrounding gaseous environment to be measured by the sensor, said optical resonator being configured to be sensitive to heat exchanges with the surrounding gaseous environment,
said at least one optical resonator comprising
at least one waveguide,
at least one introduction device for introducing a measurement light beam into the waveguide,
at least one collector configured to collect a detection light beam coming from the at least one waveguide, and
at least one heater for heating said at least one optical resonator.

2. The heat flux sensor according to claim 1, wherein the at least one heater is located away from the at least one optical resonator.

3. The heat flux sensor according to claim 2, wherein a distance separating the at least one heater and the at least one optical resonator is between 200 nm and 10 μm.

4. The heat flux sensor according to claim 2, wherein the at least one heater is a Joule effect heater.

5. The heat flux sensor according to claim 2, wherein the at least one heater comprises at least one conductive wire suspended on said support, the wire being connected to a source of electrical voltage or of electrical current.

6. The heat flux sensor according to claim 2, wherein the at least one heater comprises at least one layer of electrical resistance material located facing the at least one optical resonator and arranged on the support, the at least one layer of electrical resistance material being connected to a source of electrical voltage or of electrical current.

7. The heat flux sensor according to claim 1, wherein the at least one heater comprises a light beam source configured to introduce a light beam into the at least one optical resonator and whose power causes self-heating of the at least one optical resonator.

8. The heat flux sensor according to claim 1, wherein the suspension element comprises at least one beam.

9. The heat flux sensor according to claim 8, wherein the beam has a width between 50 nm and 10 μm with a thickness of between 50 nm and 500 nm and a length between 1 μm and 100 μm.

10. The heat flux sensor according to claim 1, wherein the at least one optical resonator comprises an optical ring, an optical disk, or a photonic crystal.

11. The heat flux sensor according to claim 10, wherein the at least one optical resonator comprises a ring of radius between 1 μm and 100 μm.

12. The heat flux sensor according to claim 1, wherein
the at least one introduction device comprises a waveguide, and
the at least one collector comprises the waveguide of the at least one introduction device, said at least one collector collecting a reflected light beam.

13. The heat flux sensor according to claim 1, wherein
the at least one introduction device comprises a waveguide, and
the heat flux sensor further comprises a second collector comprising a waveguide which is different from the waveguide of the at least one introduction device, said second collector collecting a transmitted light beam.

14. The heat flux sensor according to claim 1, wherein
the at least one introduction device comprises a waveguide,
the at least one collector, which collects a reflected light beam, comprises the waveguide of the at least one introduction device, and
said heat flux sensor also comprises another waveguide configured to collect a transmitted light beam.

15. A gas sensor comprising at least one heat flux sensor according to claim 1, wherein the at least one optical resonator is suspended in a fluid channel between an input supplying a gas e to the fluid channel and an output removing said gas mixture from the fluid channel.

16. A sensor forming a Pirani gauge comprising at least one heat flux sensor according to claim 1, wherein the at least one optical resonator is suspended in a gas mixture whose pressure the heat flux sensor is configured to measure.

17. A measurement system comprising at least one heat flux sensor according to claim 1, a measurement light beam emitter of a measurement light beam connected to the at least one introduction device, at least one photodetector connected to the at least one collector and electronics for processing signals emitted by the photodetector.

18. The measurement system according to claim 17, wherein the measurement light beam emitter emits an amplitude-modulated beam.

19. The measurement system according to claim 17, wherein the measurement light beam emitter comprises a laser.

20. The measurement system according to claim 17, wherein the measurement light beam emitter allows self-heating of the at least one optical resonator.

21. A measurement system including plural as sensors according to claim 15, wherein the gas mixture comprises a carrier gas and at least one analyte to be detected, the fluid channel of one of the gas sensors being supplied with the gas mixture and the fluid channel of another one of the gas sensors being supplied with the carrier gas alone, the at least one collector of each gas sensor being connected via a photodetector to processing electronics configured to make a differential measurement.

22. A measurement system including two gas sensors according to claim 15, and wherein the gas mixture comprises a carrier gas and at least one analyte to be detected, the fluid channel of one of the gas sensors being supplied with a gas mixture and the fluid channel of the other gas sensor being supplied with the carrier gas alone, each gas sensor including a second collector connected, via a recovery and interference device for the measurement light beams emerging from the two gas sensors, to processing electronics configured to measure phase-shift between the detection light beams collected by the two second collectors and to make an interference measurement.

23. The heat flux sensor according to claim 1, wherein the at least one suspension element comprises holes.

24. The heat flux sensor according to claim 1, wherein the at least one heater is located in a plane of the at least one optical resonator.

25. The heat flux sensor according to claim 1, wherein the at least one heater in a plane parallel to a plane of the at least one cal resonator and comprises an area such that a projection of the at least one optical resonator is completely included in the area of the at least one heater.

* * * * *